United States Patent [19]

Brantigan

[11] Patent Number: 5,425,772
[45] Date of Patent: Jun. 20, 1995

[54] PROSTHETIC IMPLANT FOR INTERVERTEBRAL SPINAL FUSION

[76] Inventor: John W. Brantigan, 13405 Parker Cir., Omaha, Nebr. 68154

[21] Appl. No.: 123,191

[22] Filed: Sep. 20, 1993

[51] Int. Cl.⁶ ............................................. A61F 2/44
[52] U.S. Cl. .................................... 623/17; 606/61
[58] Field of Search ............................. 623/17; 606/61

[56] References Cited

U.S. PATENT DOCUMENTS

| | | | |
|---|---|---|---|
| 4,349,921 | 9/1982 | Kuntz | 623/17 |
| 4,501,269 | 2/1985 | Bagby . | |
| 4,743,256 | 5/1988 | Brantigan | 623/17 |
| 4,834,757 | 5/1989 | Brantigan | 623/17 |
| 4,878,915 | 11/1989 | Brantigan | 623/17 |
| 4,961,740 | 10/1990 | Ray | 606/61 |
| 5,015,247 | 5/1991 | Michelson | 606/61 |
| 5,147,402 | 9/1992 | Bohler et al. | 623/16 |
| 5,192,327 | 3/1993 | Brantigan | 623/17 |
| 5,320,644 | 6/1994 | Baumgartner | 623/17 |

FOREIGN PATENT DOCUMENTS

| | | | |
|---|---|---|---|
| 1007661 | 3/1983 | U.S.S.R. | 606/61 |
| 1175464 | 8/1985 | U.S.S.R. | 606/61 |
| 1424826 | 9/1988 | U.S.S.R. | 606/61 |
| 1650114 | 5/1991 | U.S.S.R. | 606/61 |

*Primary Examiner*—David H. Willse
*Attorney, Agent, or Firm*—Hill, Steadman & Simpson

[57] ABSTRACT

Block or plug implants provide weight-bearing support for adjacent vertebrae in a vertebral column while allowing sufficient area between and beside the plugs for packing of autologous bone graft to allow bony healing and fusion. The plugs have a laterally directed slot to allow ingrowth of blood supply from the side and to allow locking the permanent device in place with living bone. The plugs have a patterned surface to grip the vertebrae. Plugs used for fusion in the L4-5 and L5-S1 levels are wedged-shaped to reproduce the normal shape of these discs, which are higher anteriorly than posteriorly. The height of the plugs is greater than the width. The implants are made of a biocompatible carbon fiber reinforced polymer or alternately made of traditional orthopaedic implant materials such as chrome cobalt, stainless steel or titanium. In the surgical procedure, undamaged annulus fibrous disc tissue connecting the adjacent vertebrae is preserved and a pair of side-by-side implant plugs are forced into side-by-side transverse channels in the adjoining vertebrae to stretch the remaining annulus and support body weight applied through the vertebrae. The plugs are bottomed in the channels on cortex bone and bone ingrowth and fusion is facilitated by packing a patient's own graft into the center of the plug and beside and between the two adjacent plugs.

11 Claims, 3 Drawing Sheets

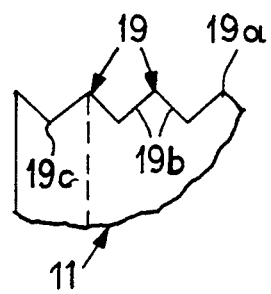
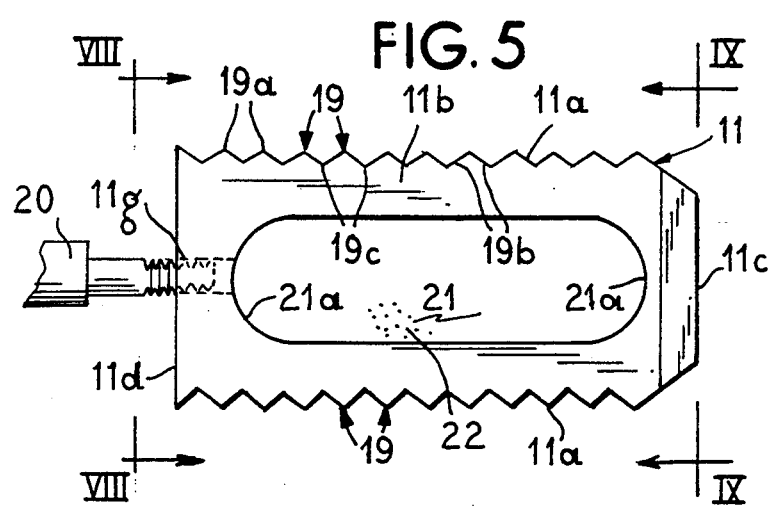
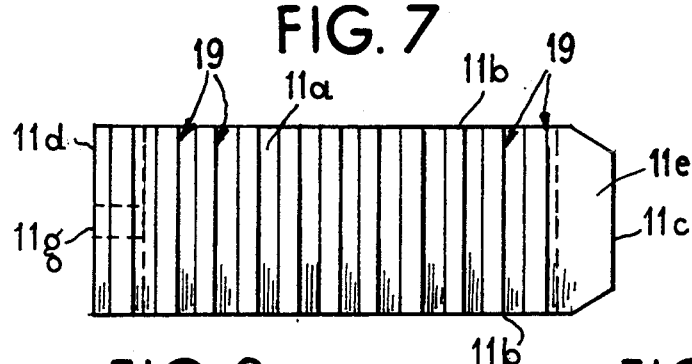
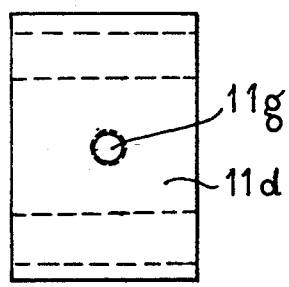
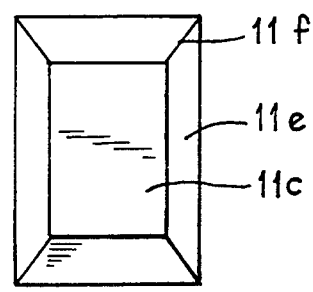

PROSTHETIC IMPLANT FOR INTERVERTEBRAL SPINAL FUSION

BACKGROUND OF THE INVENTION

1. Field of the Invention

This invention relates to the art of prosthetic devices implanted between adjacent vertebrae to treat or prevent back or neck pain in patients with ruptured or degenerated intervertebral discs. More specifically, the invention deals with improvements in prosthetic strut forming plugs or blocks facilitating bone ingrowth from adjoining vertebrae which are rectangular or, specifically, parallelepiped shaped, with height greater than width providing substantial wide roughened top and bottom surface areas for supporting adjacent vertebrae while having narrower smooth sides to minimize damaging surgical exposure and nerve root retraction required during their surgical implantation. The plugs have a horizontal or lateral slot providing a receptacle for packing bone graft material, have tapered leading ends, a tool receiving trailing end and are composed of radiolucent rigid inert material for visualization of post operative bone healing.

2. Description of the Prior Art

As pointed out in my U.S. Pat. Nos. 4,743,256, 4,834,757, 4,878,915, and 5,192,327, the leading cause of low back pain arises from rupture or degeneration of lumbar intervertebral discs. Pain in the lower extremities (sciatica) is caused by the compression of spinal nerve roots by damaged discs between the vertebrae and low back pain is caused by collapse of the disc and the adverse effects of bearing the majority of the body weight through a damaged unstable vertebral joint.

Disc excision with posterior lumbar interbody fusion (PLIF) reconstructs the normal anatomic relationships between the bony and the neural structures and has many advantages. Weight-bearing through a solid bony fusion mass between vertebral bodies relieves the mechanical pain of the traditional unstable degenerative disc and generally prevents long-term disc collapse or further degenerative changes. The complete disc excision prevents recurrent herniation of the same degenerated disc.

However, this PLIF procedure has several serious disadvantages in that it is technically very difficult, and, therefore not as successful or widely used as it might be. It requires interbody bone grafting to achieve both a strut-like support that bears the entire body's weight through the vertebral bodies, and it requires bony healing of the grafted bone to achieve permanent fusion.

It is well understood in orthopaedic surgery that grafted bone heals by a process known as "creeping substitution" in which blood capillaries first grow into the grafted bone, the grafted bone is reabsorbed, and then new bone cells are laid down along the bony matrix of the graft. During the time that the bone graft is being reabsorbed, the weight-bearing strength is reduced at least 50%, causing crushing of the graft and failure of the surgery.

My prior aforesaid U.S. Pat. No. 4,743,256 discloses an improved surgical method for eliminating spinal back pain caused by ruptured or degenerated vertebral discs by spanning the disc space between adjacent vertebrae with rigid inert implants having surfaces facilitating bone ingrowth and bottomed on prepared sites of the vertebrae to integrate the implant with the vertebrae and to provide a permanent weight supporting strut maintaining the disc space.

My prior aforesaid U.S. Pat. No. 4,878,915 disclosed a further improved surgical procedure by providing the rigid implants or blocks with tool receiving end spaces facilitating their insertion onto the prepared sites and having geometric patterns of roughened surfaces on the peripheries of the implants enhancing the bone growth.

My prior aforesaid U.S. Pat. No. 4,834,757 discloses a further improved prosthetic implant having recesses in the form of through slots be packed with bone graft material.

My prior aforesaid U.S. Pat. No. 5,192,327 describes stackable oval implants for anterior lumbar interbody fusion or vertebral reconstruction of fracture or tumor.

The Bagby U.S. Pat. No. 4,501,269 discloses a cylindrical basket seated in a cylindrical hole bored transversely across the bones of a spinal joint of a bone which permits free rocking rotation between bone and basket and only communicates bone fragments packed in the basket through perforations in the basket. Nothing was provided to lock the basket against rotation and blood supply was limited by the perforations.

The Ray U.S. Pat. No. 4,961,740 discloses a cylindrical dowel-plug implant with a screw-thread surface to be threaded into a cylindrical drilled hole in the vertebrae. While this hollow implant permitted packing of bone graft material therein, it had very small perforations limiting ingrowth of blood supply and inhibiting bony healing. The device, being cylindrical and seated in a cylindrical hole, allowed relative rotation or rocking which inhibited or destroyed bone fusion.

The Michelson U.S. Pat. No. 5,015,247 also disclosed cylindrical dowel shaped plug implants in cylindrical drilled holes in vertebrae permitting rotation and a relative movement between the plug and vertebrae during healing. Bone graft material packed within the plug could only communicate with the vertebrae through small holes limiting blood supply and bone ingrowth.

The present invention now further improves this art by providing inert narrow rectangular or parallelepiped plugs or blocks implanted in mating grooves or channels of adjacent vertebrae in spaced side-by-side relation with imperforate continuous top and bottom faces providing a greater area of weight bearing support and an interior adapted to be fully packed with bone growth material fully exposed to the vertebrae without intervening obstructions. The narrow width dimension of the plug minimizes the widths of the plug receiving grooves, provides more spacing from adjacent nerves and increases the graft bone areas. The weight bearing top and bottom surfaces or faces are roughened preferably serrated, to provide teeth for biting into the vertebrae. The plugs also have smooth side faces to prevent damage to adjacent bone faces and to facilitate insertion. The invention includes wedge shaped plugs or blocks for restoring normal spinal alignment especially in the lower lumbar levels.

SUMMARY OF THE INVENTION

The present invention now provides rigid inert, narrow vertebral prosthetic implant plugs or blocks which are higher than wide, have imperforate top and bottom weight bearing surfaces with serrations or projecting peaks that bite into adjoining vertebrae surfaces, smooth side faces which will not damage adjacent vertebrae surfaces and an unimpeded open side lateral window or slot for bone graft material in full communication with the space between adjacent vertebrae which can also be packed with bone graft material. The top and bottom weight bearing spaces are preferably transversely serrated providing teeth to bite into the vertebrae and adjoining valleys to accommodate bone ingrowth.

The narrow plugs need only be about 7 to 9 mm wide and because their weight bearing top and bottom faces are not slotted they will provide increased weight bearing areas even though they are narrower than vertically slotted plugs.

Typical plugs or blocks will have heights of 8.5 to 12.5 mm and preferably supplied three sizes of 8.5; 10.5; or 12.5 mm.

Typical teeth or serrations projecting from the weight bearing surfaces will have heights of 0.75 to 1.5 mm with spaces between the peaks of 2 to 2.5 mm.

Typical plug lengths will be 21 to 25 mm and preferably supplied in three sizes of 21, 23, or 25 mm.

A typical horizontal or laterally directed slot or window through the plug will extend substantially the full length of the plug and be wide or high enough to provide top and bottom struts of about 2.5 to 3.5 mm. The ends of the slot are spaced inwardly from the leading and trailing ends of the plug to provide strong rigid strut support with widths from 3 to 6 mm.

The plugs have a peripherally tapered leading end or nose sloping about 30 degrees from the sides and top and bottom faces of the plug.

Wedge-shaped plugs for the lumbar L4-5 and L5-S1 levels of the human spinal column are also provided by this invention. These plugs are higher anteriorly than posteriorly to allow restoration of normal disc contour and sagittal plane alignment. This is very important for the lower two lumbar discs, L4-5 and L5-S1.

Typical posterior heights for the wedge shaped plugs are 8.5 to 12.5 mm, preferably supplied in three sizes of 8.5, 10.5, or 12.5 mm. Typical heights for the anterior ends of the plug are 11 to 15 mm in three sizes of 11, 13 or 15 mm. This provides a typical 2.0 mm wedge effect.

The bone graft is packed between and beside two adjacent implants in full communication with their horizontal or lateral side slots which are also packed with bone graft material. The slots allow blood supply to grow from the sides to the bone between the two implants.

The implants are preferably made of a radiolucent material such as carbon fiber reinforced polymer such as PEEK (polyetherether ketone) or Ultrapek (polyether ketone ether ketone ketone). Alternately polycarbonate, polypropylene, polyethylene, or polysulfone types filed with glass or carbon fibers can be used. These materials are supplied by ICI Industries of Wilmington, Del., Fiber-Rite Corporation of Winona, Minn., or BASF. Other orthopaedic implant materials such as stainless steel, titanium, and chrome cobalt are useful.

PREFERRED EMBODIMENTS

Preferred embodiments of the invention are illustrated in annexed drawings in which:

FIG. 1 is a side-elevational view of the lower portion of a human vertebral column with parts broken away and shown in section to illustrate narrow flat-sided rectangular or parallelepiped prosthetic implant plugs or blocks of this invention inserted in rectangular grooves or channels in the opposed faces of adjoining vertebrae with maximum top and bottom support areas bottomed in the grooves and smooth faced side areas with a horizontal window or slot filled with bone graft and supporting the vertebrae in place of the human disc therebetween which has been partially excised to remove damaged and herniated tissue and to supply grafted bone to be reabsorbed by the vertebrae for accelerated fusion of the adjoining vertebrae.

FIG. 5 is a side elevational view of the implant plug of FIG. 4.

FIG. 6 is a fragmentary enlarged detailed view of the support area serrations or teeth of the implant plug of FIG. 5.

FIG. 7 is a top plan view of the implant plug of FIGS. 4 and 5.

FIG. 8 is an end view along the line VIII—VIII of FIG. 5.

FIG. 9 is an end view along the line IX—IX of FIG. 5.

Figure 10:
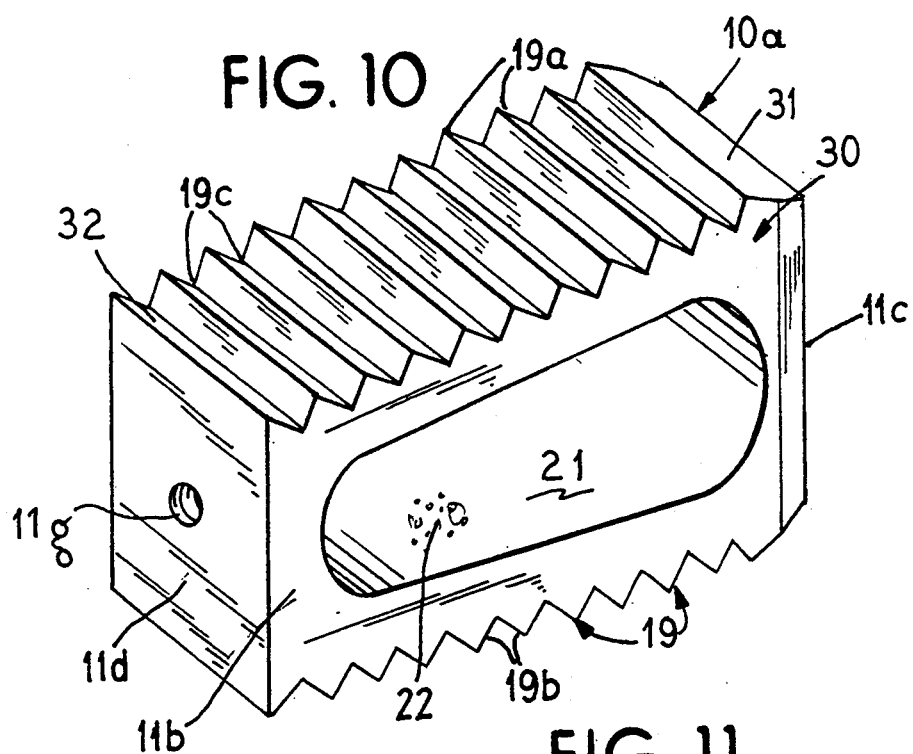
FIG. 10 is a perspective view of an alternative wedge block configuration for the implant plug of this invention.
Figure 11:
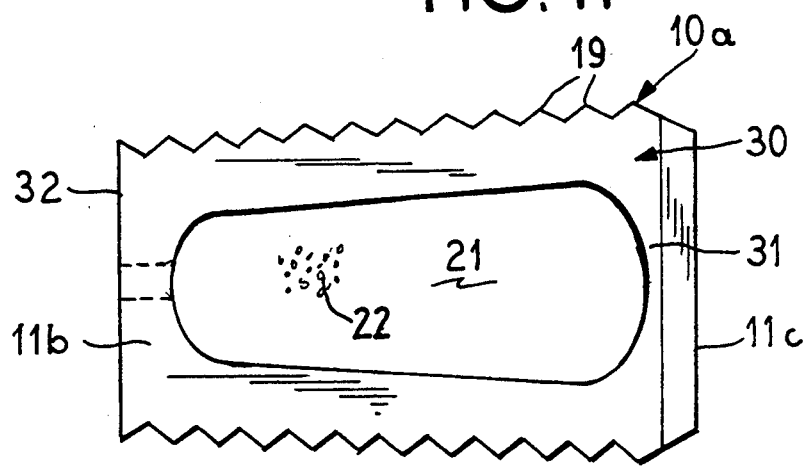
Figure 12:
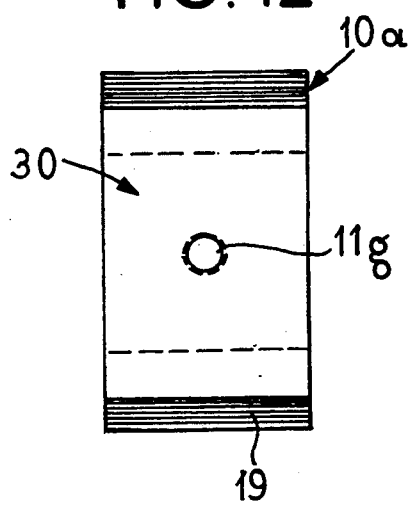
Figure 13:
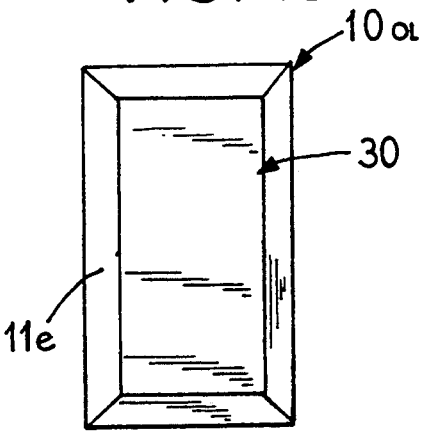

FIG. 11 is a side view of the wedge block of FIG. 10.
FIG. 12 is a left hand end-view of FIG. 11.
FIG. 13 is a right hand end-view of FIG. 11.

DESCRIPTION OF THE PREFERRED EMBODIMENTS

Figure 1:
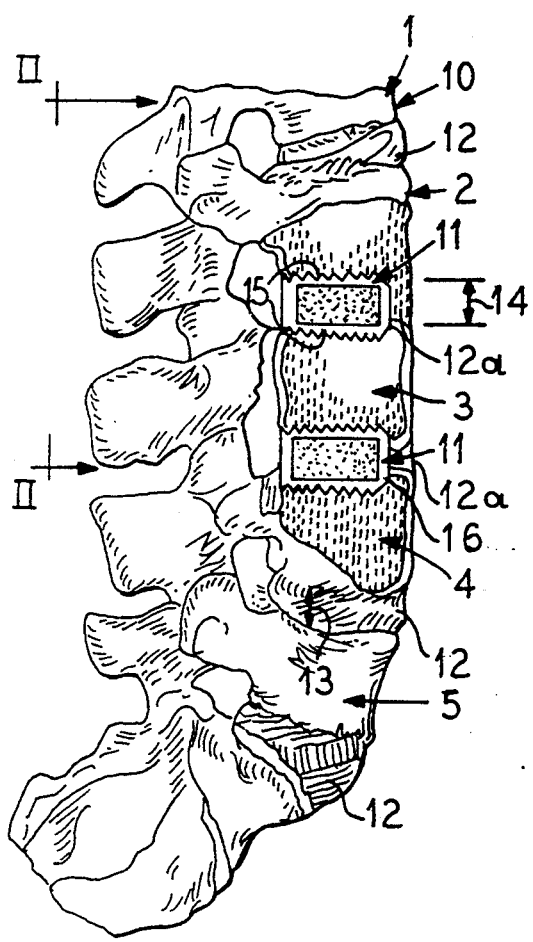
Figure 2:
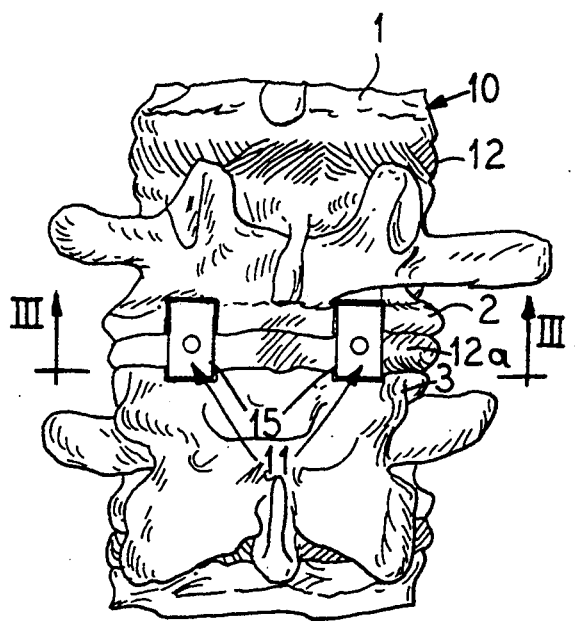
FIG. 2 is a posterior elevational view of a portion of FIG. 1 taken along the line II—II of FIG. 1.
Figure 3:
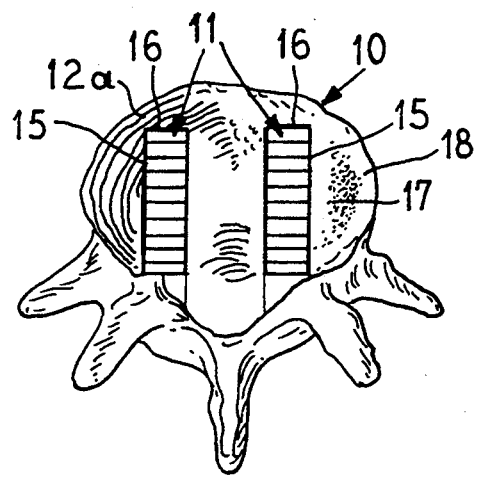
FIG. 3 is a transverse sectional view, with parts in elevation and broken away in section, along the line III—III of FIG. 2.
Figure 4:
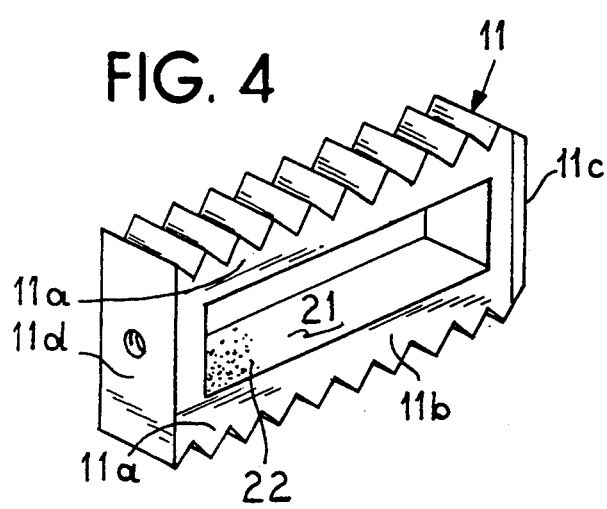
FIG. 4 is a perspective view of a preferred form of permanent implant plug of this invention.

In FIGS. 1-3, the reference numeral 10 illustrates generally the lower portion of a human vertebrae column with adjacent vertebrae supported on prosthetic implant blocks or plugs 11 of this invention.

In FIG. 1, the vertebral column 10 shows the five lower vertebrae Nos. 1-5. Adjacent vertebrae Nos. 2 and 3 and adjacent vertebrae Nos. 3 and 4 are separated by and supported on the prosthetic implant blocks or plugs 11 of this invention. Vertebrae Nos. 1 and 2 and vertebrae Nos. 4 and 5 are illustrated as supported on and separated by healthy or undamaged human discs 12 maintaining a disc space 13 between the adjoining vertebrae.

Damaged portions of the natural human discs 12 have been excised from the vertebrae Nos. 2 and 3 and Nos. 3 and 4 with the discs spaces 14 being maintained by the implant blocks or plugs 11. It is preferred to retain as much as possible of the healthy annulus tissue of the discs 12 between the vertebrae so that the remaining disc tissue 12a will at least partially surround the implants and will be held under tension by these implants. However some of the remaining disc tissue may have to be excised to open up spaces for the implant plugs.

The opposed faces of adjoining vertebrae with damaged discs therebetween have aligned flat sided rectangular channels or grooves 15 cut therein transversely of the axis of column 10. These traverse channels 15 are sufficiently deep and wide to span the central soft cancellous bone and include the hard cortex bone of the adjacent vertebrae. The undamaged human disc 12a remaining between the vertebrae is also cut or trimmed to received the implants 11 so that as much healthy annulus fibrous tissue as is available will surround the implants.

The preferred flat sided rectangular channels have blind ends 16 to be abutted by the implants 11.

As shown in FIGS. 2 and 3, the implants 11 are in the form of pair of side by side rectangular (specifically parallelepiped) plugs inserted endwise into the transverse channels 15. These channels have flat bottoms and side walls to snugly embrace the top and bottom ends or faces and the side faces of the rectangular plugs. The soft cancellous bone of the vertebrae is illustrated at 17 in FIG. 3 and is surrounded by the hard cortex bone 18. The channels 15 include portions of this hard cortex bone so that the implants span the soft cancellous bone and rest on the hard cancellous bone 18.

The channels 15 can be formed by a mortise cutting chisel tool and in the event disc tissue 12a blocks the paths for the plugs 11, tissue can be trimmed or spread apart to open up the paths.

The implant plugs or blocks as pointed out above, are rigid, inert, solid, rectangular (parallelepiped), narrow, higher than wide and longer than high as explained above. These blocks 11 have flat, continuous unslotted tops and bottoms 11a, flat smooth sides 11b, a flat front end wall 11c, and a flat back end wall 11d. The front wall 11c is beveled to a reduced rectangular nose surrounded by flat sided tapered walls 11e with corners 11f. The back end wall 11d has an internally threaded blind axial hole 11g at the center of the wall.

The tops and bottoms 11a of the plug are continuous and unslotted with traverse teeth or serrations 19 thereacross. These teeth have sharp peaks 19a with slopping side walls 19b diverging to the surfaces 11 and providing valleys 19c between the peaks. The peaks 19a will bite into the adjoining vertebrae faces when the plugs are installed while the valleys 19c can receive bone implant material or remain open for bone ingrowth.

In the surgical procedure the adjoining vertebrae are tensioned to stretch the fibrous disc tissue between the channel cut vertebrae. Slots are cut in the tissue to register with the channels 15. It is preferred to remove the nucleus pulposus from the damaged disc 12 leaving an annulus of fibrous tissue connecting the adjoining vertebrae and surrounding the inserted blocks 11. An insertion tool 20 is threaded into the threaded tapped end hole 11g of the back end wall 11d of the block 11.

The plug 11 has a single horizontal slot 21 through the longitudinal axis thereof with unimpeded open ends in the smooth side faces 11b of the plug. The horizontal slot is generally rectangular in shape and may have rounded ends 21a. The slot preferably has a height about one-third the height of the block and a length extending close to the front and rear ends 11c and 11d of the block. The thickness of these ends at the slot are sufficient to provide rigid connecting legs which will maintain the height of the plug under full loads of the vertebrae under even the most adverse conditions.

The slot 21 is packed with bone graft material 22. This bone graft material is also packed between and beside the plugs and around the plugs in the disc space between the vertebrae.

The teeth 19 preferably extend across the full widths of the tops and bottoms 11a of the plug to provide saw-like serrations firmly biting into the opposed flat bottoms of the channels 15. During the surgical procedure the disc space between the adjoining vertebrae is increased preferably beyond the height of the plug when bottomed in the channels or grooves and the smooth sides 11b of the plug will slide into the channels without damaging the side faces of the grooves. The insertion tool 20 can thus gently guide the plug into its position in the grooves and because the plugs are narrow the grooves or channels receiving them can be of reduced width providing more space between adjoining nerves of the vertebrae thereby greatly facilitating the surgical technique.

After the plugs are seated in their grooves or channels the tension load induced by stretching the vertebrae can be released permitting the stretched disc material to pull the vertebrae faces toward each other causing them to engage the sharp teeth or serration to firmly anchor the plug in position and bottom it firmly on the bottoms of the channels or grooves. The teeth will be firmly anchored to prevent any relative movement between the vertebrae and the plugs during healing. The beveled leading end of the plug facilitates insertion of the plug in proper position into the receiving channels or grooves of the vertebrae. The insertion tool is removed from the threaded hole 11g of the plug when the plug is properly seated in the vertebrae channels or grooves.

In the modified embodiment 10a shown in FIGS. 10-13 the same reference numerals applied to the FIGS. 1-9 embodiment are used to identify the same portions of the plug. However in the embodiment 10a the plug 30 is formed into a wedge shape with an anterior end 31 higher than the posterior end 32 providing a wedge effect which will permit the posterior ends of the channels or grooves cut into the adjoining vertebrae to be pulled closer together than the anterior sides of the vertebrae. The channels, however, are cut to the same depth as described above for the plugs 10 so that when the tension load on the spaced apart adjoining vertebrae is released the opposed vertebrae faces can be pulled together into full seated engagement with the plug, allowing restoration of the normal disc contour and sagittal plane alignment. This feature is important for the lower two lumbar disc, L4-5 and in the L5-S1. In the surgical procedure a noose like suture may be used to pull the opposed faces of the vertebrae toward each other into full biting engagement with the entire length of the plug.

Although the invention has been described with respect to preferred embodiments, it is not to be so limited as changes and modifications can be made which are within the full intended scope of the invention as defined by the appended claims.

I claim as my invention:

1. A surgical prosthetic device adapted to maintain normal disc space between adjoining vertebrae in a spinal column having transverse posterior to anterior open ended flat sided channels with bottoms of uniform depth along their lengths cut in the end faces of the adjoining vertebrae adapted to provide an unimpeded supply of bone graft material facilitating fusing the vertebrae together which comprises, a rigid rectangular wedge shape block defined by top, bottom, side and end walls, said block being higher than wide and longer than high, said top and bottom walls being imperforate and oriented to converge from the anterior to the posterior ends of the channels and permit the vertebrae receiving the block in the channels to be pulled together to restore normal disc contour and sagittal plane alignment, said side walls of the block being smooth to prevent irritation of the sides of the channels, said side walls having a slot providing a chamber to receive bone growth material packed around the block, one of said end walls of the block having a tool receiving recess facilitating insertion of the block into the channels, and said top and bottom walls of the block having teeth for biting into the bottoms of the channels.

2. The device of claim 1 wherein the wedge shaped block has an anterior end about 2 mm higher than the posterior end.

3. The device of claim 1 wherein the block has a posterior height of about 8.5 to 12.5 mm and an anterior height of about 11 to 15 mm.

4. A surgical prosthetic device adapted for fusing together spaced adjoining vertebrae on opposite sides of the disc in a spinal column prepared with a pair of laterally spaced posterior to anterior rectangular channels of uniform depth along their lengths providing side and bottom walls which comprises, an inert narrow rigid wedge shaped plug higher than wide and longer than high, said plug defined by top, bottom, side, and end walls, said top and bottom walls of the plug being imperforate and having means for locking with the bottom walls of adjoining vertebrae, said top and bottom walls of the plug also being inclined for converging toward the posterior ends of the channels, said side walls of the plug having a slot therethrough for receiving bone growth material facilitating fusion of the plug to the adjoining vertebrae, and said plug having a tool receiving portion facilitating insertion of the plug between the adjoining vertebrae with the top and bottom walls of the plug bottomed on the bottom walls of the channels of said adjoining vertebrae and with the incline of said top and bottom walls of the plug permitting the vertebrae to be pulled together to restore normal disc contour and to maintain sagittal alignment of the vertebrae.

5. The device of claim 4 wherein the means for locking are teeth adapted to bite into the adjoining vertebrae.

6. The device of claim 4 wherein the slot extends longitudinally of the plug.

7. The device of claim 4 wherein the side walls of the plug are smooth.

8. The device of claim 4 wherein the tool receiving portion is a recess in an end wall of the plug.

9. A pair of wedge shaped prosthetic devices adapted for fusing together spaced adjoining vertebrae in a spinal column prepared with a pair of laterally spaced posterior to anterior rectangular channels in their adjoining faces with each said pair of devices having an imperforate support function separate from a fusion function which comprises, a pair of wedge shaped inert rigid plugs defined by top, bottom, side and end walls, each of said plugs being substantially narrower than high and longer than high, said top and bottom walls having surfaces for engaging the bottoms of the channels and being oriented to converge along their length toward the posterior end of the channels receiving the plug, said side walls having smooth flat faces with bone growth receiving windows configured to face the sides of the channels, and one of said end walls of each plug having a tool receiving recess facilitating insertion of the plug in its channels.

10. The device of claim 9 wherein the window of each plug is a slot through the plug.

11. The device of claim 9 wherein the windows are provided by a horizontal slot through the plug.

* * * * *